(12) United States Patent
Hanamura et al.

(10) Patent No.: US 6,372,755 B2
(45) Date of Patent: Apr. 16, 2002

(54) STABLE MEDICINAL COMPOSITIONS CONTAINING 4,5-EPOXYMORPHINAN DERIVATIVES

(75) Inventors: Nobuyuki Hanamura; Yasuhide Horiuchi; Ryoji Yoshii; Takao Aoki; Michio Hara, all of Kanagawa (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 09/254,650

(22) PCT Filed: Jul. 10, 1998

(86) PCT No.: PCT/JP98/03096

§ 371 Date: Apr. 19, 1999

§ 102(e) Date: Apr. 19, 1999

(87) PCT Pub. No.: WO99/02158

PCT Pub. Date: Jan. 21, 1999

(30) Foreign Application Priority Data

Jul. 11, 1997 (JP) .............................................. 9-186950

(51) Int. Cl.[7] .............................................. A61K 31/44
(52) U.S. Cl. ...................................................... 514/282
(58) Field of Search .......................................... 514/282

(56) References Cited

U.S. PATENT DOCUMENTS 5,948,389 A * 9/1999 Stein ........................... 424/45

FOREIGN PATENT DOCUMENTS

| DE | 29719704 U1 | 2/1997 |
| EP | 361680 | 8/1989 |
| EP | 577847 A1 | 1/1993 |
| JP | 2693 A | 1/1990 |

OTHER PUBLICATIONS

Toru Hara, "Practical Drug Additives (in Japanese)" Mar. 5, 1974, pp. 29–32; 47–52; 217–223; and 259–261.

* cited by examiner

Primary Examiner—William R. A. Jarvis
(74) Attorney, Agent, or Firm—Birch, Stewart, Kolasch & Birch, LLP

(57) ABSTRACT

A stable pharmaceutical composition includes a 4,5-epoxymorphinan derivative, and includes at least one of the group consisting of a water soluble antioxidant, a fat soluble antioxidant, a synergist, a sugar, and a surfactant.

13 Claims, No Drawings

STABLE MEDICINAL COMPOSITIONS CONTAINING 4,5-EPOXYMORPHINAN DERIVATIVES

This application is the national phase under 35 U.S.C. § 371 of PCT International Application No. PCT/JP98/03096 which has an International filing date of Jul. 10, 1998, which designated the United States of America.

TECHNICAL FIELD

The present invention relates to a stable pharmaceutical composition including 4,5-epoxy-morphinan derivative or pharmacologically acceptable acid-addition salts thereof. More particularly, the present invention relates to a stable pharmaceutical composition including 4,5-epoxy-morphinan derivative which includes 4,5-epoxy-morphinan derivative as an effective component and includes a water soluble antioxidant, a fat soluble antioxidant, a synergist, a sugar, or a surfactant, and also relates to a method for stabilizing the pharmaceutical composition.

BACKGROUND ART

Morphine has a significant analgesic effect and is indicated for conditions such as postoperative pain and cancer pain. However, the drug has severe adverse reactions such as being addictive and causing respiratory depression and constipation, which induces clinical problems. Therefore, morphine is an analgesic which demands meticulous care.

Recently, it has become clear that opiate receptors may be classified into three types, that is, μ, δ, and κ receptor, which function as central analgesic receptors. In addition, an opiate σ receptor has also been elucidated which affects mental function.

The severe adverse reactions accompanied by administration of morphine are specific to the μ receptor agonist and to the σ receptor agonist. The δ receptor agonist and the κ receptor agonist seem not to show the above-mentioned adverse reactions.

A 4,5-epoxy-morphinan derivative does not induce the severe adverse reactions accompanied by the administration of morphine. In addition, the 4,5-epoxy-morphinan derivative is agonistic to the κ receptor or to the δ receptor, and shows significant analgesic and diuretic activities. Furthermore, the 4,5-epoxy-morphinan derivative does not show cross-tolerance with morphine or the like, and does not show an affinity for the σ receptor. Therefore, the 4,5-epoxy-morphinan derivative is a promising analgesic and a promising diuretic (WO93/15081).

However, the 4,5-epoxy-morphinan derivatives are chemically unstable to heat, light, and oxygen. Thus, means such as low-temperature storage, light protection, and displacement by an inert gas are necessary to store them.

Therefore, it is significantly useful that a stable pharmaceutical preparation including these 4,5-epoxy-morphinan derivatives is prepared.

With respect to a conventional stabilizing method for morphine, that is, a morphinan derivative, for example, in Japanese Unexamined Patent Publication No. 2-160719, an attempt to improve stability of a pharmaceutical preparation is made by adding a basic component to morphine. In addition, a stabilized pharmaceutical composition (DE29719704) or the like is known in which an antioxidant such as sodium thiosulfate or tocopherol is accompanied by naloxone. However, with respect to a 4,5-epoxy-morphinan derivative, a stabilized composition and a method of stabilization therefore has not been determined heretofore.

An object of the present invention is to provide a stable pharmaceutical composition including a 4,5-epoxy-morphinan derivative and also to provide a method for stabilizing it.

DISCLOSURE OF INVENTION

The present invention relates to a pharmaceutical composition including a 4,5-epoxy-morphinan derivative and at least one substance selected from the group consisting of the following materials (1), (2), (3), (4) and (5).

(1) A water soluble antioxidant selected from the group consisting of sodium sulfite, sodium hydrogensulfite, sodium pyrosulfite, Rongalite, L-ascorbic acid, erysorbic acid, sodium thiosulfate, sodium thiomalate, cysteine, thioglycerol, and hydroxyquinoline sulfate.

(2) A fat soluble antioxidant selected from the group consisting of propyl gallate, butyl hydroxytoluene, butyl hydroxyanisole, tocopherol, ascorbyl palmitate, ascorbyl stearate, nordihydroguaiaretic acid, and mercaptobenzimidazole.

(3) A synergist selected from the group consisting of EDTA, salts thereof, citric acid, salts thereof, and lecithin.

(4) A sugar selected from the group consisting of D-mannitol, D-sorbitol, xylitol, glucose, and fructose.

(5) A surfactant selected from the group consisting of sorbitan sesquioleate, sorbitan laurate, sorbitan palmitate, glyceryl myristate, polyoxyethylene nonylphenyl ether, and polyoxyethylene lauryl ether.

BEST MODE FOR CARRYING OUT THE INVENTION

The present invention relates to stable pharmaceutical compositions including a 4,5-epoxy-morphinan derivative and at least one component selected from the group consisting of a water soluble antioxidant, a fat soluble antioxidant, a synergist, a sugar, and a surfactant.

A 4,5-epoxy-morphinan derivative in accordance with the present invention can be prepared by the method disclosed in WO93/15081 and is a compound represented by the general formula (I) or pharmacologically acceptable acid-addition salts thereof:

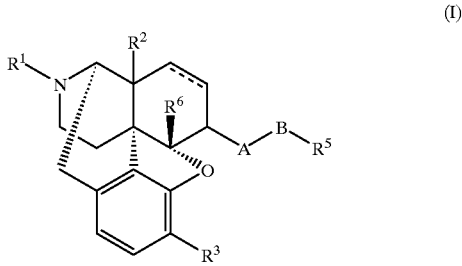

wherein - - - is a double bond or a single bond; $R^1$ is an alkyl group having from 1 to 5 carbon atoms, a cycloalkylalkyl group having from 4 to 7 carbon atoms, a cycloalkenylalkyl group having from 5 to 7 carbon atoms, an aryl group having from 6 to 12 carbon atoms, an aralkyl group having from 7 to 13 carbon atoms, an alkenyl group having from 4 to 7 carbon atoms, an allyl group, a furan-2-ylalkyl group having from 1 to 5 carbon atoms, or a thiophene-2-ylalkyl group having from 1 to 5 carbon atoms; $R^2$ is a hydrogen atom, a hydroxy group, a nitro group, an alkanoyloxy group having from 1 to 5 carbon atoms, an alkoxy group having from 1 to 5 carbon atoms, an alkyl group having from 1 to 5 carbon atoms, or —$NR^7R^8$; $R^7$ is a hydrogen atom or an alkyl group having from 1 to 5 carbon atoms; $R^8$ is a hydrogen atom, an alkyl group having from 1 to 5 carbon atoms, or —C(=O)$R^9$; $R^9$ is a hydrogen atom, a phenyl group, or an alkyl group having from 1 to 5 carbon atoms; $R^3$ is a hydrogen atom, a hydroxy group, an alkanoyloxy group having from 1 to 5 carbon atoms, or an alkoxy group having from 1 to 5 carbon atoms; A is —$N(R^4)C(=X)$—, —$N(R^4)C(=X)Y$—, —$N(R^4)$—, or —$N(R^4)SO_2$— (wherein X and Y are, independently of one another, $NR^4$, S, or O; and $R^4$ is a hydrogen atom, a straight-chain or branched-chain alkyl group having from 1 to 5 carbon atoms, or an aryl group having from 6 to 12 carbon atoms; and $R^4$ may be identical or different in the formula); B is a valence bond, a straight-chain or branched-chain alkylene group having from 1 to 14 carbon atoms (wherein the alkylene group may be substituted with one or more substituents selected from the group consisting of an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, a trifluoromethyl group, a trifluoromethoxy group and a phenoxy group, and wherein one to three methylene groups of the alkylene group may be replaced with carbonyl groups), a straight-chain or branched-chain acyclic unsaturated hydrocarbon containing from one to three double bonds and/or triple bonds and having from 2 to 14 carbon atoms (wherein the acyclic unsaturated hydrocarbon may be substituted with one or more substituents selected from the group consisting of an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, a trifluoromethyl group, a trifluoromethoxy group and a phenoxy group, and wherein one to three methylene groups of the acyclic unsaturated hydrocarbon may be replaced with carbonyl groups), or a straight-chain or branched-chain saturated or unsaturated hydrocarbon containing from one to five thioether, ether and/or amino bonds and having from 1 to 14 carbon atoms (wherein no hetero atoms are bonded directly to A, and one to three methylene groups of the hydrocarbon may be replaced with carbonyl groups); and $R^5$ is a hydrogen atom or an organic group having a basic skeleton selected from the group consisting of following formulas:

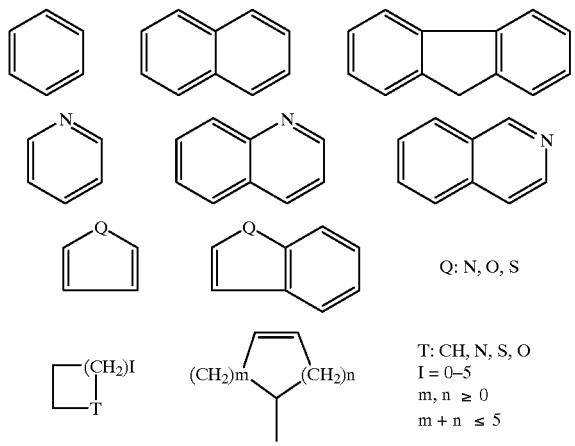

Organic Groups Represented by $R^5$ wherein the organic group may have at least one substituent selected from the group consisting of an alkyl group having from 1 to 5 carbon atoms, an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, an isothiocyanate group, a trifluoromethyl group, a trifluoromethoxy group, and a methylenedioxy group; $R^6$ is a hydrogen atom, an alkyl group having from 1 to 5 carbon atoms or an alkanoyl group having from 1 to 5 carbon atoms.

In the general formula (I), $R^1$ is preferably a methyl group, an ethyl group, a propyl group, a butyl group, an isobutyl group, a cyclopropylmethyl group, an allyl group, a benzyl group, or a phenethyl group, and more preferably a cyclopropylmethyl group or an allyl group.

$R^2$ and $R^3$ are preferably a hydrogen atom, a hydroxy group, an acetoxy group, or a methoxy group, independently.

A is preferably —$N(R^4)C(=O)$—, —$N(R^4)C(=O)O$—, —$N(R^4)$—, or —$N(R^4)SO_2$— (wherein $R^4$ is a hydrogen atom, or a straight-chain or branched-chain alkyl group having from 1 to 5 carbon atoms). Among them A is more preferably —$N(R^4)C(=O)$— or —$N(R^4)C(=O)O$— (wherein $R^4$ is a hydrogen atom, or a straight-chain or branched-chain alkyl group having from 1 to 5 carbon atoms).

B is preferably a straight-chain alkylene group having from 1 to 3 carbon atoms, —CH=CH—, —C≡C—, —$CH_2O$— or —$CH_2S$—. Among them, B is more preferably a straight-chain alkylene group having from 1 to 3 carbon atoms, —CH=CH—, or —C≡C—.

$R^5$ is preferably a hydrogen atom or an organic group having a basic skeleton selected from the group consisting of the following basic formulas:

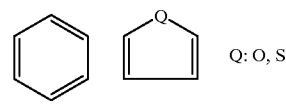

Organic Groups Represented by $R^5$ wherein the organic group may be substituted with one or more substituents selected from the group consisting of an alkyl group having from 1 to 5 carbon atoms, an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, an isothiocyanate group, a trifluoromethyl group, a trifluoromethoxy group, and a methylenedioxy group.

$R^6$ is preferably a hydrogen atom.

17-(cyclopropyl methyl)-3,14β-dihydroxy-4,5α-epoxy-6β-[N-methyl-trans-3-(3-furyl)acrylamide]morphinan hydrochloride (hereinafter referred to as "Compound 1") and 17-(cyclopropyl methyl)-3,14β-dihydroxy-4,5α-epoxy-6β-[N-methyl-3-(4-trifluoromethylphenyl)propiolamide]morphinan hydrochloride (hereinafter referred to as "Compound 2") are particularly preferred.

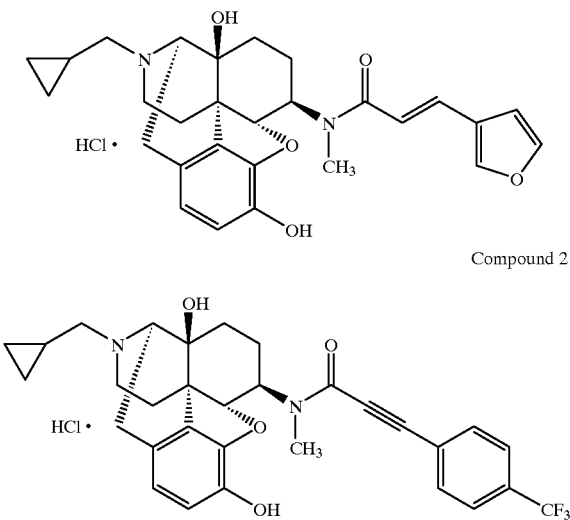

Compound 1

Compound 2

The pharmacologically acceptable acid-addition salts thereof are inorganic acid salts, such as chlorides, sulfates, nitrates, hydrobromides, hydroiodides, and phosphates; organic carboxylates, such as acetates, lactates, citrates, oxalates, glutarates, malates, tartrates, fumarates, mandelates, maleates, benzoates, and phthalates; and organic sulfonates, such as methanesulfonates, ethanesulfonates, benzenesulfonates, p-toluenesulfonates, and camphor-sulfonates. Among them, chlorides, hydrobromides, phosphates, tartrates, malates, and methanesulfonates are preferred, but of course the pharmacologically acceptable acid-addition salts thereof are not limited to these compounds.

With respect to a composition content of the 4,5-epoxymorphinan derivative, that is, an effective component, any content may be available, even if the content of the effective component in a pharmaceutical composition is sufficient for a treatment. For example, the content may range from 0.01 to 10000 μg/pharmaceutical composition. Ordinarily, the content preferably ranges from 0.1 to 1000 μg/pharmaceutical composition.

In the present invention, sulfites, nitrites, ascorbic acids, thiol derivatives, hydroxyquinoline sulfate, or the like is used as a water soluble antioxidant. Phenolic compounds, fat soluble vitamins, ascorbic acid esters, fat soluble vitamins, nordihydroguaiaretic acid, mercaptobenzimidazole, or the like is used as a fat soluble antioxidant. EDTA, salts thereof, citric acid, salts thereof, lecithin, or the like is used as a synergist. The above-mentioned synergist shows a weak antioxidant effect by itself. However, the effect can be increased in combination with other antioxidants.

Specifically, a sulfite such as sodium sulfite, sodium hydrogensulfite, sodium pyrosulfite, or Rongalite, a nitrite such as sodium nitrite, a ascorbic acid such as L-ascorbic acid or erysorbic acid, and a thiol derivative such as sodium thiosulfate, sodium thiomalate, cysteine, thioglycerol, or hydroxyquinoline sulfate is used as a water soluble antioxidant. Among them, sodium thiosulfate is most preferable.

A phenolic compound such as propyl gallate, butyl hydroxytoluene, or butyl hydroxyanisole, a fat soluble vitamin such as tocopherol or a fat soluble vitamin such as ascorbyl palmitate, ascorbyl stearate, nordihydroguaiaretic acid, or mercaptobenzimidazole is used as a fat soluble antioxidant. Among them, propyl gallate, butyl hydroxytoluene or butyl hydroxyanisole is preferable.

For example, EDTA, salts thereof, citric acid, salts thereof, lecithin, or the like is used as a synergist. With respect to salts, sodium salts, calcium salts, potassium salts, or magnesium salts are preferable. Among them, EDTA or citric acid is more preferable.

At least one selected from the group consisting of above-described water soluble antioxidants, fat soluble antioxidants, and synergists is used as an antioxidant. In addition, at least one sugar or at least one surfactant can be mixed therein.

The content of the antioxidant ranges from 0.00001 to 10 percent by weight of the total pharmaceutical composition, preferably ranges from 0.001 to 10 percent by weight of the total pharmaceutical composition, and more preferably 0.001 to 1 percent by weight of the total pharmaceutical composition.

It is confirmed that the antioxidant is sufficiently effective when it is solved or dispersed in a solution, or when it is dispersed in a semisolid or in a solid. The antioxidant is effective for stabilization of all dosage forms such as syrups, powders, fine granules, granules, tablets, hard capsules, soft capsules, injections, freeze-drying dosage forms, ointments, tapes, lotions, nose drops, ophthalmic solutions, aerosols, suspensions, emulsions, plasters, and suppositories.

Specifically, a sugar used in the present invention, for example, is D-mannitol, D-sorbitol, xylitol, glucose, maltose, fructose, sucrose, or white soft sugar.

Preferably, D-mannitol, D-sorbitol, xylitol, glucose, or fructose is used alone or used in a mixture of at least two thereof. Furthermore, at least one of water soluble antioxidants, fat soluble antioxidants, synergists, and surfactants can be mixed therein.

The content of the sugar ranges from 0.01 to 20 percent by weight of the total pharmaceutical composition, preferably ranges from 0.1 to 20 percent by weight of the total pharmaceutical composition, and more preferably 1 to 20 percent by weight of the total pharmaceutical composition.

It is confirmed that addition of sugars is particularly useful for stabilization of injections. In addition, it has been shown that when a water soluble antioxidant, a fat soluble antioxidant, or a synergist as an antioxidant is added, a greater stabilization effect can be obtained. Among them, D-mannitol, D-sorbitol, xylitol, and glucose are useful for stabilization of the injections. With respect to the accompanying antioxidant, sodium thiosulfate, that is, a water soluble antioxidant and citric acid, that is, a synergist, are particularly preferable.

Specifically, a surfactant used in the present invention, for example, is sorbitan sesquioleate, sorbitan laurate, sorbitan palmitate, glyceryl myristate, polyoxyethylene nonylphenyl ether, and polyoxyethylene lauryl ether.

Preferably, glyceryl myristate or polyoxyethylene nonylphenyl ether is used alone or used as a mixture of at least two thereof. Furthermore, at least one of water soluble antioxidants, fat soluble antioxidants, synergists, and sugars can be mixed therein.

The content of the surfactant ranges from 0.0001 to 20 percent by weight of the total pharmaceutical composition, preferably ranges from 0.001 to 20 percent by weight of the total pharmaceutical composition, and more preferably 0.01 to 10 percent by weight of the total pharmaceutical composition.

It is confirmed that addition of the surfactant is particularly useful for stabilization of external preparations such as ointments, gels, tapes, lotions, nose drops, ophthalmic solutions, aerosols, and suppositories. In addition, it is shown that when a water soluble antioxidant, a fat soluble antioxidant, or a synergist as an antioxidant is added, a greater stabilization effect can be obtained. Among them, glyceryl myristate and polyoxyethylene nonylphenyl ether are useful for stabilization of the external preparations. With respect to the accompanying antioxidant, citric acid, that is, a synergist, is particularly preferable.

An available additive such as vehicles, binders, thickener, solubilizer, solvents, isotonizing agents, buffers, preservatives, or bases may be added to the pharmaceutical compositions in accordance with the present invention, if necessary.

The additives in the present invention are not particularly limited, even though they are pharmaceutically acceptable. Examples of a vehicle are lactose, white soft sugar, sucrose, sorbitol, microcrystalline cellulose, corn starch, gelatin, dextrans and the like. Examples of a binder are hydroxypropylcellulose, hydroxypropylmethylcellulose, polyvinyl pyrrolidone, methyl cellulose, and the like. Examples of a thickener are gum arabic, sodium hyaluronate, xanthan gum, and the like. Examples of a solvent are water, ethanol, propylene glycol, polyethylene glycol, Polysorbate 80, glycerin, soybean oil and the like. Examples of an isotonizing agent are sodium chloride, D-mannitol, xylitol, glucose and the like. Examples of a solubilizer are cyclodextrin and the like. Examples of a nonionic surfactant are polyoxyethylene hydrogenated castor oil, sorbitan sesquioleate, sorbitan laurate, sorbitan palmitate, glyceryl oleate, glyceryl myristate, polyoxyethylene lauryl ether, polyoxyethylene nonylphenyl ether, and the like. Examples of a buffer are tartaric acid, citric acid, maleic acid, phosphoric acid, succinic acid, lactic acid, acetic acid, sodium hydrogencarbonate, boric acid, sodium borate, magnesium oxide, magnesium hydroxide, and the like. Examples of a preservative are methyl paraoxybenzoate, ethyl paraoxybenzoate, propyl paraoxybenzoate, butyl paraoxybenzoate, benzalkonium chloride, and the like. Examples of a base are white petrolatum, Witepsol, Plastibase, liquid paraffin, and the like.

The pharmaceutical compositions in accordance with the present invention are not particularly limited, even though they have pharmaceutically acceptable dosage forms for administration. The pharmaceutical compositions in accordance with the present invention are available for all dosage forms such as syrups, powders, fine granules, granules, tablets, hard capsules, soft capsules, injections, freeze-drying dosage forms, ointments, gels, tapes, lotions, nose drops, ophthalmic solutions, aerosols, suspensions, emulsions, plasters, and suppositories.

EXAMPLES

Advantages of the present invention will become clear from the following description of examples. However, it is to be understood that the invention is not limited thereto.

Example 1

In measuring flasks, aqueous solutions containing Compound 1 (10 μg/mL) which were added a predetermined concentration of a variety of antioxidants, and an aqueous solution containing the compound with no additives were prepared. Test 1, Test 2, and Comparative Example are shown in Table 1.

TABLE 1

| Example 1 | Dosage Form | Drug Content | Antioxidant | Additive Rate |
|---|---|---|---|---|
| Comparative Example | Aqueous solution | 10 μg/mL | None | |
| Test 1 | Aqueous solution | 10 μg/mL | Citric acid | 0.10% |
| Test 2 | Aqueous solution | 10 μg/mL | Sodium thiosulfate | 0.10% |

Stability test: The aqueous solutions of Test 1, Test 2, and Comparative example were sealed in ampoules. Then, after storing them at a temperature of 80° C. for five days, the concentrations of Compound 1 were measured using a HPLC method (an UV method). The residual rates were calculated, so that stability of the aqueous solutions was estimated.

TABLE 2

| Example 1 | Antioxidant | Additive Rate | Storage Conditions | Residual Rate (%) |
|---|---|---|---|---|
| Comparative Example | None | | Seal/80° C./5 d | 41.4 |
| Test 1 | Citric acid | 0.10% | Seal/80° C./5 d | 93.5 |
| Test 2 | Sodium thiosulfate | 0.10% | Seal/80° C./5 d | 90.8 |

As shown in Table 2, the residual rates of Test 1 and Test 2 to which the antioxidant was added by 0.1% were higher than that of Comparative Example to which no antioxidant was added, so that a significant stabilizing effect on Compound 1 was shown.

Example 2

As shown in Prescription Example 1, injections were prepared by adding a predetermined amount of an isotonizing agent to Compound 1 (10 μg/mL). Tests 1 to 4 and Comparative Example are shown in Table 3.

(Prescription Example 1)

Injection

| Compound 1 | 1 mg |
|---|---|
| Isotonizing agent | 0.9 to 5 g |
| Water for injection | Balance volume |
| Total | 100 mL |

TABLE 3

| Example 2 | Dosage Form | Drug Content | Isotonizing Agent | Additive Rate |
|---|---|---|---|---|
| Comparative Example | Injection | 10 μg/mL | Sodium chloride | 0.90% |
| Test 1 | Injection | 10 μg/mL | Glucose | 5.00% |
| Test 2 | Injection | 10 μg/mL | Xylitol | 5.00% |
| Test 3 | Injection | 10 μg/mL | Mannitol | 5.00% |
| Test 4 | Injection | 10 μg/mL | D-sorbitol | 5.00% |

Stability test: After the aqueous solutions of Tests 1 to 4, and Comparative Example were subjected to nitrogen bubbling, they were sealed in ampoules. Then, after storage at a temperature of 80° C. for seven days, the residual rates of Compound 1 were measured using a HPLC method (an UV method). Thus, stability after accelerated storage was estimated.

TABLE 4

| Example 2 | Isotonizing Agent | Additive Rate | Storage Conditions | Residual Rate (%) |
|---|---|---|---|---|
| Comparative Example | Sodium chloride | 0.90% | Seal/80° C./7 d | 66.6 |
| Test 1 | Glucose | 5.00% | Seal/80° C./7 d | 90.3 |
| Test 2 | Xylitol | 5.00% | Seal/80° C./7 d | 97.9 |
| Test 3 | Mannitol | 5.00% | Seal/80° C./7 d | 98.9 |
| Test 4 | D-sorbitol | 5.00% | Seal/80° C./7 d | 97.4 |

As shown in Table 4, the residual rates of Tests 1 to 4 were significantly higher than that of Comparative Example to which sodium chloride as the isotonizing agent was added. Therefore, with respect to the accelerated storage of the injections, sugars as isotonizing agents showed significant stabilizing effects on Compound 1.

Example 3

As shown in Prescription Example 2, injections were prepared by adding a predetermined amount of sodium thiosulfate to a 5% aqueous solution of mannitol containing Compound 1 (10 μg/mL) and a injection to which no sodium thiosulfate was added was also prepared. Tests 1 to 3 and Comparative Example are shown in Table 5.

(Prescription Example 2)

Injection

| Compound 1 | 1 mg |
|---|---|
| Sodium thiosulfate | 0 to 1 g |
| Mannitol | 5 g |
| Water for injection | Balance volume |
| Total | 100 mL |

TABLE 5

| Example 3 | Dosage Form | Drug Content | Antioxidant | Additive Rate |
|---|---|---|---|---|
| Comparative Example | Injection | 10 μg/mL | None | |
| Test 1 | Injection | 10 μg/mL | Sodium thiosulfate | 0.10% |
| Test 2 | Injection | 10 μg/mL | Sodium thiosulfate | 0.50% |
| Test 3 | Injection | 10 μg/mL | Sodium thiosulfate | 1.00% |

Stability test: The aqueous solutions of Tests 1 to 3, and that of Comparative Example were sealed in ampoules. Then, after sterilization by heating at a temperature of 120° C. for 60 minutes, the purities of Compound 1 in the samples were measured using a HPLC method (an UV method). Thus, pharmaceutical stability after sterilization was estimated.

TABLE 6

| Example 3 | Antioxidant | Additive Rate | Storage Conditions | Purity (%) |
|---|---|---|---|---|
| Comparative Example | None | | Seal/120° C./60 min | 98.95 |
| Test 1 | Sodium thiosulfate | 0.10% | Seal/120° C./60 min | 99.57 |
| Test 2 | Sodium thiosulfate | 0.50% | Seal/120° C./60 min | 99.44 |
| Test 3 | Sodium thiosulfate | 1.00% | Seal/120° C./60 min | 99.53 |

As shown in Table 6, the purities of Tests 1 to 3 were significantly higher than that of Comparative Example to which no antioxidant was added. With respect to the sterilization process of the injections, sodium thiosulfate showed a significant stabilizing effect on Compound 1. The difference of the effects due to the amounts of the sodium thiosulfate was not seen in the range of 0.1 to 1.0%, and any additive amount showed the same stabilizing effect.

Example 4

Aqueous solutions containing Compound 1 and a predetermined amount of antioxidants, or an aqueous solution, to which no antioxidant was added, were added dropwise and mixed to a mixture of lactose and Avicel PH101, so that granulated substances were obtained. After drying the above-mentioned substances at a temperature of 40° C. for 12 hours, so that the granules shown in Prescription Example 3 were prepared. Tests 1 to 9 and Comparative Example are shown in Table 7.

(Prescription Example 3)

Granule

| Compound 1 | 100 mg |
|---|---|
| Sodium thiosulfate | 0 to 1 g |
| Avicel PH-101 | 31 g |
| Lactose | Balance volume |
| Total | 100 g |

TABLE 7

| Example 4 | Dosage Form | Drug Content | Antioxidant | Additive Rate |
|---|---|---|---|---|
| Comparative Example | Granule | 100 μg/100 mg | None | |
| Test 1 | Granule | 100 μg/100 mg | EDTA | 0.10% |
| Test 2 | Granule | 100 μg/100 mg | Citric acid | 0.10% |
| Test 3 | Granule | 100 μg/100 mg | Propyl gallate | 0.10% |
| Test 4 | Granule | 100 μg/100 mg | Butyl Hydroxyanisole | 0.10% |
| Test 5 | Granule | 100 μg/100 mg | Tocopherol | 0.10% |
| Test 6 | Granule | 100 μg/100 mg | Sodium thiosulfate | 0.10% |
| Test 7 | Granule | 100 μg/100 mg | Sodium thiosulfate | 0.20% |
| Test 8 | Granule | 100 μg/100 mg | Sodium thiosulfate | 0.50% |
| Test 9 | Granule | 100 μg/100 mg | Sodium thiosulfate | 1.00% |

Stability test: Immediately after manufacturing the granules of Tests 1 to 9 and that of Comparative Example, the purities of Compound 1 were measured using a HPLC method (an UV method). Thus, pharmaceutical stability was estimated.

TABLE 8

| Example 4 | Antioxidant | Additive Rate | Storage Conditions | Purity (%) |
|---|---|---|---|---|
| Comparative Example | None | | Immediately after Manufacturing | 98.48 |
| Test 1 | EDTA | 0.10% | Immediately after Manufacturing | 98.75 |
| Test 2 | Citric acid | 0.10% | Immediately after Manufacturing | 98.56 |
| Test 3 | Propyl gallate | 0.10% | Immediately after Manufacturing | 99.33 |
| Test 4 | Butyl Hydroxyanisole | 0.10% | Immediately after Manufacturing | 98.62 |
| Test 5 | Tocopherol | 0.10% | Immediately after Manufacturing | 99.20 |
| Test 6 | Sodium thiosulfate | 0.10% | Immediately after Manufacturing | 99.49 |
| Test 7 | Sodium thiosulfate | 0.20% | Immediately after Manufacturing | 99.49 |
| Test 8 | Sodium thiosulfate | 0.50% | Immediately after Manufacturing | 99.30 |
| Test 9 | Sodium thiosulfate | 1.00% | Immediately after Manufacturing | 98.99 |

As shown in Table 8, the purities of the compound in the granules of Tests 1 to 9 were significantly higher than that of Comparative Example to which no antioxidant was added. Thus, the stabilizing effects on Compound 1 were also shown in the granules. In addition, when the difference of the effects due to the amounts of the sodium thiosulfate was studied in Tests 6 to 9, the highest stabilizing effect can be seen in the range of 0.1 to 0.2%.

Example 5

Aqueous solutions containing Compound 1 and a predetermined amount of antioxidants, or an aqueous solution, to which no antioxidant was added, were added dropwise and mixed to a mixture of lactose, Avicel PH101, and HPC-SL, so that granulated substances were obtained. After drying the above-mentioned substances at a temperature of 40° C. for 12 hours, sieving them, mixing with magnesium stearate, and compressing tablets, the tablets shown in Prescription Example 4 were prepared. Tests 1 and Comparative Example are shown in Table 9.

(Prescription Example 4)

Tablet

| | |
|---|---|
| Compound 1 | 100 mg |
| Sodium thiosulfate | 0 to 1 g |
| Avicel PH-101 | 30 g |
| HPC-SL | 3 g |
| Magnesium stearate | 0.5 g |
| Lactose | Balance volume |
| Total | 100 g |

TABLE 9

| Example 5 | Dosage Form | Drug Content | Antioxidant | Additive Rate |
|---|---|---|---|---|
| Comparative Example | Tablet | 100 µg/tablet | None | |

TABLE 9-continued

| Example 5 | Dosage Form | Drug Content | Antioxidant | Additive Rate |
|---|---|---|---|---|
| Test 1 | Tablet | 100 µg/tablet | Sodium thiosulfate | 0.10% |

Stability test: After the tablets of Test 1 and Comparative Example were sealed in bottles, they were stored at a temperature of 40° C. and at a relative humidity (R.H.) by 75% for three months. Then, the residual rates were measured using a HPLC method (an UV method), so that pharmaceutical stability was estimated.

TABLE 10

| Example 5 | Antioxidant | Additive Rate | Storage Conditions | Purity (%) |
|---|---|---|---|---|
| Comparative Example | None | | Seal/40° C./75% R.H./3 m | 98.12 |
| Test 1 | Sodium thiosulfate | 0.10% | Seal/40° C./75% R.H./3 m | 99.20 |

As shown in Table 10, the residual rates of Test 1 was higher than that of Comparative Example to which no antioxidant was added, so that with respect to a tablet, a significant stabilizing effect on Compound 1 was also seen.

Example 6

Aqueous solutions containing Compound 1 and a predetermined amount of antioxidants, or an aqueous solution, to which no antioxidant was added, were dissolved in Polyethylene glycol 400, so that filling fluids for soft capsules shown in Prescription Example 5 were prepared. Tests 1 to 3 and Comparative Example are shown in Table 11.

(Prescription Example 5)

Filling Fluid For Soft Capsules

| | |
|---|---|
| Compound 1 | 40 mg |
| Sodium thiosulfate | 0 to 0.1 g |
| Purified water | 2 g |
| Polyethylene glycol 400 | Balance volume |
| Total | 100 g |

TABLE 11

| Example 6 | Dosage Form | Drug Content | Antioxidant | Additive Rate |
|---|---|---|---|---|
| Comparative Example | Filling fluid for soft capsules | 40 µg/100 mg | None | 0.00% |
| Test 1 | Filling fluid for soft capsules | 40 µg/100 mg | Sodium thiosulfate | 0.01% |
| Test 2 | Filling fluid for soft capsules | 40 µg/100 mg | Sodium thiosulfate | 0.05% |
| Test 3 | Filling fluid for soft capsules | 40 µg/100 mg | Sodium thiosulfate | 0.10% |

Stability test: After the filling fluids for the soft capsules of Test 1 to 3 and that of Comparative Example were sealed in ampoules, the filling fluids for the soft capsules were stored at a temperature of 80° C. for one week. Then, the residual rates of compound 1 were measured using a HPLC method (an UV method), so that pharmaceutical stability of the filling fluid was estimated.

TABLE 12

| Example 6 | Antioxidant | Additive Rate | Storage Conditions | Residual Rate (%) |
|---|---|---|---|---|
| Comparative Example | None | 0.00% | Seal/80° C./1 w | 19.3 |
| Test 1 | Sodium thiosulfate | 0.01% | Seal/80° C./1 w | 23.4 |
| Test 2 | Sodium thiosulfate | 0.05% | Seal/80° C./1 w | 88.3 |
| Test 3 | Sodium thiosulfate | 0.10% | Seal/80° C./1 w | 85.1 |

As shown in Table 12, the residual rates of Test 1 to 3 were higher than that of Comparative Example to which no antioxidant was added, so that with respect to the above-described filling fluids a significant stabilizing effect on Compound 1 was shown. In addition, the difference of the effects due to the amounts of the sodium thiosulfate was studied. It has been clear that the greater the additional amount, the higher the stabilizing effect.

Example 7

The filling fluid for the soft capsules of Test 1 and that of Comparative Example were degassed by nitrogen bubbling. Then, 100 mg of the filling fluid for the soft capsule was packed in the gelatin capsule shown in Prescription Example 6, so that the soft capsule was prepared. Test 1 and Comparative Example are shown in Table 13.

(Prescription Example 6)

Gelatin Capsule For Soft Capsules

| Gelatin | 21 g |
| Gelatin succinate | 21 g |
| Glycerin | 23 g |
| Titanium oxide | 0.7 g |
| Purified water | Balance volume |
| Total | 100 g |

TABLE 13

| Example 7 | Dosage Form | Drug Content | Antioxidant | Additive Rate |
|---|---|---|---|---|
| Comparative Example | Soft capsule | 40 μg/capsule | None | 0.00% |
| Test 1 | Soft capsule | 40 μg/capsule | Sodium thiosulfate | 0.10% |

Stability test: After the capsule of Test 1 and that of Comparative Example were sealed in bottles, the capsules were stored at a temperature of 40° C. and at a R.H. by 75% for one month. Then, the residual concentrations of the drug were measured using a HPLC method (an UV method), so that stability of the soft capsule was estimated.

TABLE 14

| Example 7 | Antioxidant | Additive Rate | Storage Conditions | Residual Rate (%) |
|---|---|---|---|---|
| Comparative Example | None | 0.00% | Seal/40° C./75% R.H./1 m | 98.8 |
| Test 1 | Sodium thiosulfate | 0.10% | Seal/40° C./75% R.H./1 m | 99.1 |

As shown in Table 14, the residual rate of Test 1 was higher than that of Comparative Example to which no antioxidant was added, so that with respect to a soft capsule, a significant stabilizing effect on Compound 1 due to the antioxidant was seen.

Example 8

Hydroxypropylmethylcellulose as a gelatinizing agent, Polyethylene glycol 4000 as a humectant, and ethyl paraoxybenzoate and butyl paraoxybenzoate as preservatives were dissolved in an aqueous solution containing Compound 1 and a predetermined amount of antioxidants, or were dissolved in an aqueous solution to which no antioxidant was added. Thus, aqueous gels shown in Prescription Example 7 were prepared. Tests 1 and Comparative Example are shown in Table 15.

(Prescription Example 7)

Aqueous Gel

| Compound 1 | 1 mg |
| Hydroxypropylmethylcellulose | 2 g |
| Polyethylene glycol 4000 | 15 g |
| Sodium thiosulfate | 0 to 0.1 g |
| Ethyl paraoxybenzoate | 0.03 g |
| Butyl paraoxybenzoate | 0.02 g |
| Purified water | Balance volume |
| Total | 100 g |

TABLE 15

| Example 8 | Dosage Form | Drug Content | Antioxidant | Additive Rate |
|---|---|---|---|---|
| Comparative Example | Aqueous gel | 10 μg/g | None | 0.00% |
| Test 1 | Aqueous gel | 10 μg/g | Sodium thiosulfate | 0.10% |

Stability test: After the aqueous gel of Test 1 and that of Comparative Example were sealed in aluminized tube, the aqueous gels were stored at a temperature of 60° C. and at a R.H. by 75% for one month. Then, the purities of Compound 1 in the aqueous gels were measured using a HPLC method (an UV method), so that stability of the aqueous gel was estimated.

TABLE 16

| Example 8 | Antioxidant | Additive Rate | Storage Conditions | Purity (%) |
|---|---|---|---|---|
| Comparative Example | None | 0.00% | Seal/60° C./75% R.H./1 m | 19.3 |
| Test 1 | Sodium thiosulfate | 0.10% | Seal/60° C./75% R.H./1 m | 99.6 |

As shown in Table 16, the purity of Test 1, to which sodium thiosulfate was added at a concentration of 0.1%, was higher than that of Comparative Example, to which sodium thiosulfate was not added, during storage under a severe condition. Thus, with respect to an aqueous gel, a significant stabilizing effect on Compound 1 due to sodium thiosulfate was seen.

Example 9

As shown in Prescription Example 8, Compound 1 was dissolved in a heated surfactant, and the mixture was mixed with liquid paraffin and white petrolatum. Thus, petrolatum ointments were obtained. Tests 1 to 6 and Comparative Example are shown in Table 17.

(Prescription Example 8)

Petrolatum Ointment

| | |
|---|---|
| Compound 1 | 1 mg |
| Surfactant | 5 g |
| Liquid paraffin | 15 g |
| White petrolatum | Balance volume |
| Total | 100 g |

TABLE 17

| Example 9 | Dosage Form | Drug Content | Solubilizer | Additive Rate |
|---|---|---|---|---|
| Comparative Example | Petrolatum ointment | 10 μg/g | Glyceryl monooleate | 5.00% |
| Test 1 | Petrolatum ointment | 10 μg/g | Sorbitan sesquioleate | 5.00% |
| Test 2 | Petrolatum ointment | 10 μg/g | Sorbitan monolaurate | 5.00% |
| Test 3 | Petrolatum ointment | 10 μg/g | Sorbitan monopalmitate | 5.00% |
| Test 4 | Petrolatum ointment | 10 μg/g | Polyoxyethylene (2) lauryl ether | 5.00% |
| Test 5 | Petrolatum ointment | 10 μg/g | Glyceryl monomyristate | 5.00% |
| Test 6 | Petrolatum ointment | 10 μg/g | polyoxyethylene (3) nonylphenyl ether | 5.00% |

Stability test during manufacturing: Yields of the major degradation products (N-oxides) in the ointments of Test 1 to 6 and that of Comparative Example were measured using a HPLC method (an UV method) immediately after the preparation therefor. Thus, stability during manufacturing was estimated.

TABLE 18

| Example 9 | Solubilizer | Additive Rate | Storage Conditions | Yield of major degradation product (%) |
|---|---|---|---|---|
| Comparative Example | Glyceryl monooleate | 5.00% | Stability immediately after manufacturing | 5.6 |
| Test 1 | Sorbitan sesquioleate | 5.00% | Stability immediately after manufacturing | 1 |
| Test 2 | Sorbitan monolaurate | 5.00% | Stability immediately after manufacturing | 0.7 |
| Test 3 | Sorbitan monopalmitate | 5.00% | Stability immediately after manufacturing | 0.8 |
| Test 4 | Polyoxyethylene (2) lauryl ether | 5.00% | Stability immediately after manufacturing | 1.6 |
| Test 5 | Glyceryl monomyristate | 5.00% | Stability immediately after manufacturing | 0 |
| Test 6 | polyoxyethylene (3) nonylphenyl ether | 5.00% | Stability immediately after manufacturing | 0 |

As shown in Table 18, the yields of the major degradation products of Tests 1 to 6 were lower than that of Comparative Example to which a surfactant was added. In particular, the addition of glyceryl monomyristate or polyoxyethylene nonylphenyl, that is, Test 5 or 6, respectively, showed a significant stabilizing effect.

Example 10

As shown in Prescription Example 9, Compound 1 and citric acid were dissolved in heated glycerin monomyristate, and the mixture was mixed with liquid paraffin and white petrolatum. Thus, petrolatum ointments to which a predetermined amount of citric acid was added, and a petrolatum ointment to which citric acid was not added were obtained. Tests 1, Test 2, and Comparative Example are shown in Table 19.

(Prescription Example 9)

Petrolatum Ointment

| | |
|---|---|
| Compound 1 | 1 mg |
| Glyceryl monomyristate | 5 g |
| Citric acid | 0 to 0.1 g |
| Liquid paraffin | 15 g |
| White petrolatum | Balance volume |
| Total | 100 g |

TABLE 19

| Example 10 | Dosage Form | Drug Content | Antioxidant | Additive Rate |
|---|---|---|---|---|
| Comparative Example | Petrolatum ointment | 10 μg/g | None | — |
| Test 1 | Petrolatum ointment | 10 μg/g | Citric acid | 0.001% |
| Test 2 | Petrolatum ointment | 10 μg/g | Citric acid | 0.10% |

Stability test: After the ointments of Test 1, Test 2 and Comparative Example were sealed in aluminized tubes, the ointments were stored at a temperature of 60° C. and at a R.H. by 75% for a half month. Then, the purities of Compund 1 in the ointments were measured using a HPLC method (an UV method), so that stability of the ointment was estimated.

TABLE 20

| Example 10 | Antioxidant | Additive Rate | Storage Conditions | Purity (%) |
|---|---|---|---|---|
| Comparative Example | None | 0.00% | Seal/60° C./75% R.H./0.5 m | 89.4 |
| Test 1 | Citric acid | 0.001% | Seal/60° C./75% R.H./0.5 m | 98.4 |
| Test 2 | Citric acid | 0.10% | Seal/60° C./75% R.H./0.5 m | 96.2 |

As shown in Table 20, the purities of the drug of Tests 1 and 2 were higher than that of Comparative Example to which citric acid was not added. With respect to a petrolatum ointment, citric acid (a synergist) showed a significant stabilizing effect on Compound 1.

Example 11

As shown in Prescription Example 10, injections were prepared by adding a predetermined amount of an isotonizing agent to Compound 2 (50 μg/mL). Tests 1 to 3 and Comparative Example are shown in Table 21.

(Prescription Example 10)

Injection

| Compound 2 | 5 mg |
|---|---|
| Isotonizing agent | 0.9 to 5 g |
| Water for injection | Balance volume |
| Total | 100 mL |

TABLE 21

| Example 11 | Dosage Form | Drug Content | Isotonizing Agent | Additive Rate |
|---|---|---|---|---|
| Comparative Example | Injection | 50 μg/mL | Sodium chloride | 0.90% |
| Test 1 | Injection | 50 μg/mL | Glucose | 5.00% |
| Test 2 | Injection | 50 μg/mL | Xylitol | 5.00% |
| Test 3 | Injection | 50 μg/mL | Mannitol | 5.00% |

Stability test: The aqueous solutions of Tests 1 to 3, and that of Comparative Example were sealed in ampoules. After sterilization by high-pressure steam at a temperature of 121° C. for 30 minutes, the residual rates of Compound 2 in the samples were measured using a HPLC method (an UV method). Thus, pharmaceutical stability after sterilization was estimated.

TABLE 22

| Example 11 | Isotonizing Agent | Additive Rate | Storage Conditions | Residual Rate (%) |
|---|---|---|---|---|
| Comparative | Sodium chloride | 0.90% | Seal/121° C./30 mim | 94.7 |

TABLE 22-continued

| Example 11 | Isotonizing Agent | Additive Rate | Storage Conditions | Residual Rate (%) |
|---|---|---|---|---|
| Example Test 1 | Glucose | 5.00% | Seal/121° C./30 mim | 100.0 |
| Test 2 | Xylitol | 5.00% | Seal/121° C./30 mim | 98.0 |
| Test 3 | Mannitol | 5.00% | Seal/121° C./30 mim | 100.0 |

As shown in Table 22, the residual rates of Tests 1 to 3 were significantly higher than that of Comparative Example to which sodium chloride as an isotonizing agent was added. Therefore, with respect to the high-pressure steam sterilization process, sugars as isotonizing agents showed significant stabilizing effects on Compound 2.

Industrial Applicability

As shown in the results of the above-described examples, a pharmaceutical composition including a 4,5-epoxy-morphinan derivative in accordance with the present invention is a stable pharmaceutical preparation in which stability of the 4,5-epoxy-morphinan derivative is improved. Furthermore, the stability thereof is significantly improved by optimizing compound ratio and ingredients thereof. In addition, since a stabilization effect is seen, in spite of variations in the dosage form of the drug, it is suggested that the handling during manufacturing the drug and storing thereof can be improved, and effectiveness, stability, and handling during administration can also be improved. Furthermore, a variety of dosage forms and administration routes can be selected, and indications for treatments for various diseases can be expanded.

What is claimed is:

1. A pharmaceutical composition comprising, a 4,5-epoxy-morphinan derivative and at least one substance selected from the group consisting of the following materials (1), (2), (3), (4) and (5):

(1) a water soluble antioxidant selected from the group consisting of sodium sulfite, sodium hydrogensulfite, sodium pyrosulfite, Rongalite, sodium nitrite, L-ascorbic acid, erysorbic acid, sodium thiosulfate, sodium thiomalate, cysteine, thioglycerol, and hydroxyquinoline sulfate;

(2) a fat soluble antioxidant selected from the group consisting of propyl gallate, butyl hydroxytoluene, butyl hydroxyanisole, tocopherol, ascorbyl palmitate, ascorbyl stearate, nordihydroguaiaretic acid, and mercaptobenzimidazole;

(3) a synergist selected from the group consisting of EDTA, salts thereof, citric acid, salts thereof, and lecithin;

(4) a sugar selected from the group consisting of D-mannitol, D-sorbitol, xylitol, glucose, and fructose; and (5) a surfactant selected from the group consisting of sorbitan sesquioleate, sorbitan laurate, sorbitan palmitate, glyceryl myristate, polyoxyethylene nonylphenyl ether, and polyoxyethylene lauryl ether, wherein the 4,5-epoxy-morphinan derivative is a compound represented by the general formula (I) or pharmacologically acceptable salts thereof:

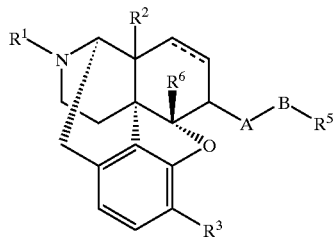

(I)

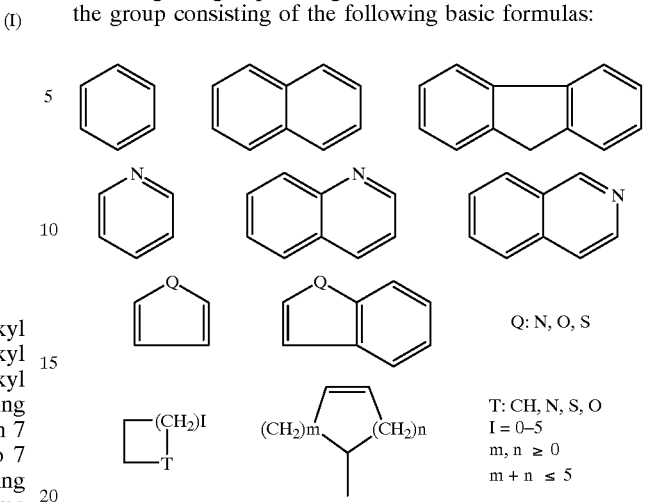

wherein - - - is a double bond, or a single bond; $R^1$ is an alkyl group having from 1 to 5 carbon atoms, a cycloalkylalkyl group having from 4 to 7 carbon atoms, a cycloalkenylalkyl group having from 5 to 7 carbon atoms, an aryl group having from 6 to 12 carbon atoms, an aralkyl group having from 7 to 13 carbon atoms, an alkenyl group having from 4 to 7 carbon atoms, an allyl group, a furan-2-ylalkyl group having from 1 to 5 carbon atoms, or a thiophene-2-ylalkyl group having from 1 to 5 carbon atoms; $R^2$ is a hydrogen atom, a hydroxy group, a nitro group, an alkanoyloxy group having from 1 to 5 carbon atoms, an alkoxy group having from 1 to 5 carbon atoms, an alkyl group having from 1 to 5 carbon atoms, or —$NR^7R^8$; $R^7$ is a hydrogen atom or an alkyl group having from 1 to 5 carbon atoms; $R^8$ is a hydrogen atom, an alkyl group having from 1 to 5 carbon atoms or —C(=O)$R^9$; $R^9$ is a hydrogen atom, a phenyl group, or an alkyl group having from 1 to 5 carbon atoms; $R^3$ is a hydrogen atom, a hydroxy group, an alkanoyloxy group having from 1 to 5 carbon atoms, or an alkoxy group having from 1 to 5 carbon atoms; A is —$N(R^4)C(=X)$—, —$N(R^4)C(=X)Y$—, —$N(R^4)$—, or —$N(R^4)SO_2$— (wherein X and Y are, independently of one another, $NR^4$, S, or O; and $R^4$ is a hydrogen atom, a straight-chain or branched-chain alkyl group having from 1 to 5 carbon atoms, or an aryl group having from 6 to 12 carbon atoms; and $R^4$ is identical or different in the formula); B is a valence bond, a straight-chain or branched chain alkylene group having from 1 to 14 carbon atoms (wherein the alkylene group is optionally substituted with one or more substituents selected from the group consisting of an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, a trifluoromethyl group, a trifluoromethoxy group and a phenoxy group, and wherein one to three methylene groups of the alkylene group is optionally replaced with carbonyl groups), a straight-chain or branched-chain acyclic unsaturated hydrocarbon containing from one to three double bonds and/or triple bonds having from 2 to 14 carbon atoms (wherein the acyclic unsaturated hydrocarbon is optionally substituted with one or more substituents selected from the group consisting of an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, a trifluoromethyl group, a trifluoromethoxy group and a phenoxy group, and wherein one to three methylene groups of the acyclic unsaturated hydrocarbon is optionally replaced with carbonyl groups), or a straight-chain or branched-chain saturated or unsaturated hydrocarbon containing from one to five thioether, ether, and/or amino bonds and having from 1 to 14 carbon atoms (wherein no hetero atoms are bonded directly to A, and one to three methylene groups of the hydrocarbon is optionally replaced with carbonyl groups); and $R^5$ is a hydrogen atom or an organic group having a basic skeleton selected from the group consisting of the following basic formulas:

organic groups represented by $R^5$
wherein the organic group has optionally at least one substituent selected from the group consisting of an alkyl group having from 1 to 5 carbon atoms, an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, an isothiocyanate group, a trifluoromethyl group, a trifluoromethoxy group, and a methylenedioxy group; $R^6$ is a hydrogen atom, an alkyl group having from 1 to 5 carbon atoms, or an alkanoyl group having from 1 to 5 carbon atoms.

2. A pharmaceutical composition according to claim 1, wherein in the general formula (I), $R^1$ is a methyl group, an ethyl group, a propyl group, a butyl group, an isobutyl group, a cyclopropylmethyl group, an allyl group, a benzyl group, or a phenethyl group; $R^2$ and $R^3$ are, independently of one another, a hydrogen atom, a hydroxy group, an acetoxy group, or a methoxy group; A is —$N(R^4)C(=O)$—, —$N(R^4)C(=O)O$—, —$N(R^4)$—, or —$N(R^4)SO_2$— (wherein $R^4$ is a hydrogen atom, or a straight-chain or branched-chain alkyl group having from 1 to 5 carbon atoms); B is a straight-chain alkylene group having from 1 to 3 carbon atoms, —CH=CH—, —C≡C—, —$CH_2O$— or —$CH_2S$—; $R^5$ is the same as in claim 1; and $R^6$ is a hydrogen atom.

3. A pharmaceutical composition according to claim 2, wherein in the general formula (I), $R^5$ is a hydrogen atom or an organic group having a basic skeleton selected from the group consisting of the following basic formulas:

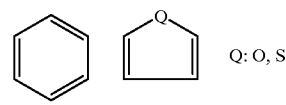

Organic Groups Represented by $R^5$
wherein the organic group is optionally substituted with one or more substituents selected from the group consisting of an alkyl group having from 1 to 5 carbon atoms, an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, an isothiocyanate group, a trifluoromethyl group, a trifluoromethoxy group, and a methylenedioxy group.

4. A pharmaceutical composition according to claim 3, wherein in the general formula (I), $R^1$ is a cyclopropylmethyl group or an allyl group; A is —N($R^4$)C(=O)— or —N($R^4$)C(=O)O— (wherein $R^4$ is a hydrogen atom, or a straight-chain or branched-chain alkyl group having from 1 to 5 carbon atoms); and B is a straight-chain alkylene group having from 1 to 3 carbon atoms, —CH=CH—, or —C≡C—.

5. The pharmaceutical composition according to any one of claims 1, 2, 3, or 4, wherein each content of the water-soluble antioxidant, the fat soluble antioxidant, and the synergist ranges from 0.00001 to 10 percent by weight of the total pharmaceutical composition.

6. An injection preparation comprising:

a compound represented by the general formula (I) or pharmacologically acceptable acid-addition salts thereof:

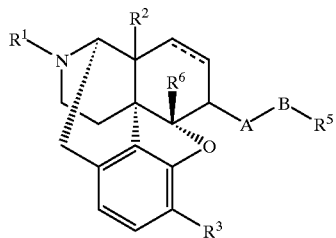

(I)

wherein - - - is a double bond or a single bond; $R^1$ is an alkyl group having from 1 to 5 carbon atoms, a cycloalkylalkyl group having from 4 to 7 carbon atoms, a cycloalkenylalkyl group having from 5 to 7 carbon atoms, an aryl group having from 6 to 12 carbon atoms, an aralkyl group having from 7 to 13 carbon atoms, an alkenyl group having from 4 to 7 carbon atoms, an allyl group, a furan-2-ylalkyl group having from 1 to 5 carbon atoms, or a thiophene-2-ylalkyl group having from 1 to 5 carbon atoms; $R^2$ is a hydrogen atom, a hydroxy group, a nitro group, an alkanoyloxy group having from 1 to 5 carbon atoms, an alkoxy group having from 1 to 5 carbon atoms, an alkyl group having from 1 to 5 carbon atoms, or —$NR^7R^8$; $R^7$ is a hydrogen atom or an alkyl group having from 1 to 5 carbon atoms; $R^8$ is a hydrogen atom, an alkyl group having from 1 to 5 carbon atoms, or —C((=O) $R^9$; $R^9$ is a hydrogen atom, a phenyl group, or an alkyl group having from 1 to 5 carbon atoms; $R^3$ is a hydrogen atom, a hydroxy group, an alkanoyloxy group having from 1 to 5 carbon atoms, or an alkoxy group having from 1 to 5 carbon atoms; A is —N($R^4$)C(=X)—, —N($R^4$)C(=X)Y—, —N($R^4$)—, or —N($R^4$)$SO_2$— (wherein X and Y are, independently of one another, $NR^4$, S, or O; and $R^4$ is a hydrogen atom, a straight-chain or branched-chain alkyl group having from 1 to 5 carbon atoms, or an aryl group having from 6 to 12 carbon atoms; and $R^4$ is identical or different in the formula); B is a valence bond, a straight-chain or branched-chain alkylene group having from 1 to 14 carbon atoms (wherein the alkylene group is optionally substituted with one or more substituents selected from the group consisting of an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, a trifluoromethyl group, a trifluoromethoxy group and a phenoxy group, and wherein one to three methylene groups of the alkylene group is optionally replaced with carbonyl groups), a straight-chain or branched-chain acyclic unsaturated hydrocarbon containing from one to three double bonds and/or triple bonds and having from 2 to 14 carbon atoms (wherein the acyclic unsaturated hydrocarbon is optionally substituted with one or more substituents selected from the group consisting of an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, a trifluoromethyl group, a trifluoromethoxy group and a phenoxy group, and wherein one to three methylene groups of the acyclic unsaturated hydrocarbon is optionally replaced with carbonyl groups), or a straight-chain or branched-chain saturated or unsaturated hydrocarbon containing from one to five thioether, ether, and/or amino bonds and having from 1 to 14 carbon atoms (wherein no hetero atoms are bonded directly to A, and one to three methylene groups of the hydrocarbon is optionally replaced with carbonyl groups); and $R^5$ is a hydrogen atom or an organic group having a basic skeleton selected from the group consisting of the following basic formulas:

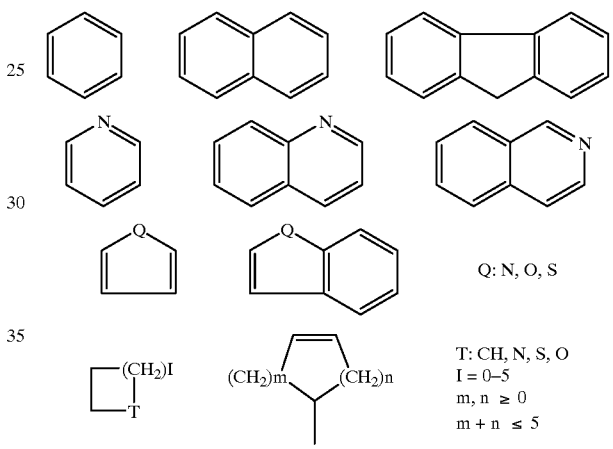

Organic Groups Represented by $R^5$ wherein the organic group has optionally at least one substituent selected from the group consisting of an alkyl group having from 1 to 5 carbon atoms, an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, an isothiocyanate group, a trifluoromethyl group, a trifluoromethoxy group, and a methylenedioxy group; $R^6$ is a hydrogen atom, an alkyl group having from 1 to 5 carbon atoms, or an alkanoyl group having from 1 to 5 carbon atoms; and at least one sugar selected from the group consisting of D-mannitol, D-sorbitol, xylitol, glucose, and fructose.

7. An injection preparation according to claim 6, further comprising, at least one substance selected from the group consisting of the following materials (1), (2), and (3):

(1) a water soluble antioxidant selected from the group consisting of sodium sulfite, sodium hydrogensulfite, sodium pyrosulfite, Rongalite, sodium nitrite, L-ascorbic acid, erysorbic acid, sodium thiosulfate, sodium thiomalate, cysteine, thioglycerol, and hydroxyquinoline sulfate;

(2) a fat soluble antioxidant selected from the group consisting of propyl gallate, butyl hydroxytoluene, butyl hydroxyanisole, tocopherol, ascorbyl palmitate, ascorbyl stearate, nordihydroguaiaretic acid, and mercaptobenzimidazole; and
(3) a synergist selected from the group consisting of EDTA, salts thereof, citric acid, salts thereof, and lecithin.

8. An external preparation comprising:
a compound represented by the general formula (I) or pharmacologically acceptable acid-addition salts thereof:

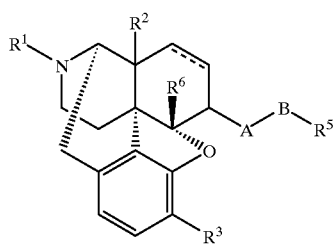

(I)

wherein - - - is a double bond or a single bond; $R^1$ is an alkyl group having from 1 to 5 carbon atoms, a cycloalkylalkyl group having from 4 to 7 carbon atoms, a cycloalkenylalkyl group having from 5 to 7 carbon atoms, an aryl group having from 6 to 12 carbon atoms, an aralkyl group having from 7 to 13 carbon atoms, an alkenyl group having from 4 to 7 carbon atoms, an allyl group, a furan-2-ylalkyl group having from 1 to 5 carbon atoms, or a thiophene-2-ylalkyl group having from 1 to 5 carbon atoms; $R^2$ is a hydrogen atom, a hydroxy group, a nitro group, an alkanoyloxy group having from 1 to 5 carbon atoms, an alkoxy group having from 1 to 5 carbon atoms, an alkyl group having from 1 to 5 carbon atoms, or —$NR^7R^8$; $R^7$ is a hydrogen atom or an alkyl group having from 1 to 5 carbon atoms; $R^8$ is a hydrogen atom, an alkyl group having from 1 to 5 carbon atoms, or —C(=O)$R^9$; $R^9$ is a hydrogen atom, a phenyl group, or an alkyl group having from 1 to 5 carbon atoms; $R^3$ is a hydrogen atom, a hydroxy group, an alkanoyloxy group having from 1 to 5 carbon atoms, or an alkoxy group having from 1 to 5 carbon atoms; A is —N($R^4$)C(=X)—, —N($R^4$)C(=X)Y—, —N($R^4$)—, or —N($R^4$)$SO_2$— (wherein X and Y are, independently of one another, $NR^4$, S, or O; and $R^4$ is a hydrogen atom, a straight-chain or branched-chain alkyl group having from 1 to 5 carbon atoms, or an aryl group having from 6 to 12 carbon atoms; and $R^4$ is identical or different in the formula); B is a valence bond, a straight-chain or branched-chain alkylene group having from 1 to 14 carbon atoms (wherein the alkylene group is optionally substituted with one or more substituents selected from the group consisting of an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, a trifluoromethyl group, a trifluoromethoxy group and a phenoxy group, and wherein one to three methylene groups of the alkylene group is optionally replaced with carbonyl groups), a straight-chain or branched-chain acyclic unsaturated hydrocarbon containing from one to three double bonds and/or triple bonds and having from 2 to 14 carbon atoms (wherein the acyclic unsaturated hydrocarbon is optionally substituted with one or more substituents selected from the group consisting of an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, a trifluoromethyl group, a trifluoromethoxy group and a phenoxy group, and wherein one to three methylene groups of the acyclic unsaturated hydrocarbon is optionally replaced with carbonyl groups), or a straight-chain or branched-chain saturated or unsaturated hydrocarbon containing from one to five thioether, ether, and/or amino bonds and having from 1 to 14 carbon atoms (wherein no hetero atoms are bonded directly to A, and one to three methylene groups of the hydrocarbon is optionally replaced with carbonyl groups); and $R^5$ is a hydrogen atom or an organic group having a basic skeleton selected from the group consisting of the following basic formulas:

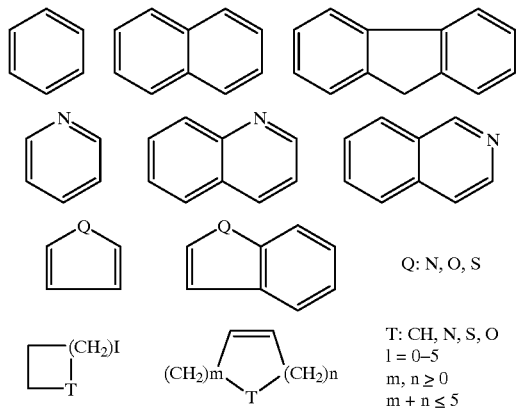

Organic Groups Represented by $R^5$
wherein the organic group has optionally at least one substituent selected from the group consisting of an alkyl group having from 1 to 5 carbon atoms, an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, an isothiocyanate group, a trifluoromethyl group, a trifluoromethoxy group, and a methylenedioxy group; $R^6$ is a hydrogen atom, an alkyl group having from 1 to 5 carbon atoms, or an alkanoyl group having from 1 to 5 carbon atoms; and at least one surfactant selected from the group consisting of sorbitan sesquioleate, sorbitan laurate, sorbitan palmitate, glyceryl myristate, polyoxyethylene nonylphenyl ether, and polyoxyethylene lauryl ether.

9. An external preparation according to claim 8, further comprising, at least one substance selected from the group consisting of the following materials (1), (2), and (3):
(1) a water soluble antioxidant selected from the group consisting of sodium sulfite, sodium hydrogensulfite, sodium pyrosulfite, Rongalite, sodium nitrite, L-ascorbic acid, erysorbic acid, sodium thiosulfate, sodium thiomalate, cysteine, thioglycerol, and hydroxyquinoline sulfate;
(2) a fat soluble antioxidant selected from the group consisting of propyl gallate, butyl hydroxytoluene, butyl hydroxyanisole, tocopherol, ascorbyl palmitate, ascorbyl stearate, nordihydroguaiaretic acid, and mercaptobenzimidazole; and
(3) a synergist selected from the group consisting of EDTA, salts thereof, citric acid, salts thereof, and lecithin.

10. A method for stabilizing a 4,5-epoxy-morphinan derivative, wherein at least one substance selected from the group consisting of the following materials (1), (2), (3), (4), and (5) is used:
  (1) a water soluble antioxidant selected from the group consisting of sodium sulfite, sodium hydrogensulfite, sodium pyrosulfite, Rongalite, sodium nitrite, L-ascorbic acid, erysorbic acid, sodium thiosulfate, sodium thiomalate, cysteine, thioglycerol, and hydroxyquinoline sulfate;
  (2) a fat soluble antioxidant selected from the group consisting of propyl gallate, butyl hydroxytoluene, butyl hydroxyanisole, tocopherol, ascorbyl palmitate, ascorbyl stearate, nordihydroguaiaretic acid, and mercaptobenzimidazole;
  (3) a synergist selected from the group consisting of EDTA, salts thereof, citric acid, salts thereof, and lecithin;
  (4) a sugar selected from the group consisting of D-mannitol, D-sorbitol, xylitol, glucose, and fructose; and
  (5) a surfactant selected from the group consisting of sorbitan sesquioleate, sorbitan laurate, sorbitan palmitate, glyceryl myristate, polyoxyethylene nonylphenyl ether, and polyoxyethylene lauryl ether,
wherein the 4,5-epoxy-morphinan composition is a compound represented by the general formula (I) or pharmacologically acceptable salts thereof:

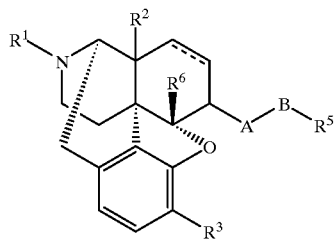

(I)

wherein - - - is a double bond, or a single bond; $R^1$ is an alkyl group having from 1 to 5 carbon atoms, a cycloalkylalkyl group having from 4 to 7 carbon atoms, a cycloalkenylalkyl group having from 5 to 7 carbon atoms, an aryl group having from 6 to 12 carbon atoms, an aralkyl group having from 7 to 13 carbon atoms, an alkenyl group having from 4 to 7 carbon atoms, an allyl group, a furan-2-ylalkyl group having from 1 to 5 carbon atoms, or a thiophene-2-ylalkyl group having from 1 to 5 carbon atoms; $R^2$ is a hydrogen atom, a hydroxy group, a nitro group, an alkanoyloxy group having from 1 to 5 carbon atoms, an alkoxy group having from 1 to 5 carbon atoms, an alkyl group having from 1 to 5 carbon atoms, or —$NR^7R^8$; $R^7$ is a hydrogen atom or an alkyl group having from 1 to 5 carbon atoms; $R^8$ is a hydrogen atom, an alkyl group having from 1 to 5 carbon atoms, or —C(=O)$R^9$; $R^9$ is a hydrogen atom, a phenyl group, or an alkyl group having from 1 to 5 carbon atoms; $R^3$ is a hydrogen atom, a hydroxy group, an alkanoyloxy group having from 1 to 5 carbon atoms, or an alkoxy group having from 1 to 5 carbon atoms; A is —N($R^4$)C(=X)—, —N($R^4$)C(=X)Y—, —N($R^4$)—, or N($R^4$)$SO_2$— (wherein X and Y are, independently of one another, N$R^4$, S, or O; and $R^4$ is a hydrogen atom, a straight-chain or branched-chain alkyl group having from 1 to 5 carbon atoms, or an aryl group having from 6 to 12 carbon atoms; and $R^4$ is identical or different in the formula); B is a valence bond, a straight-chain or branched-chain alkylene group having from 1 to 14 carbon atoms (wherein the alkylene group is optionally substituted with one or more substituents selected from the group consisting of an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, a trifluoromethyl group, a trifluoromethoxy group and a phenoxy group, and wherein one to three methylene groups of the alkylene group is optionally replaced with carbonyl groups), a straight-chain or branched-chain acyclic unsaturated hydrocarbon containing from one to three double bonds and/or triple bonds and having from 2 to 14 carbon atoms (wherein the acyclic unsaturated hydrocarbon is optionally substituted with one or more substituents selected from the group consisting of an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, a trifluoromethyl group, a trifluoromethoxy group and a phenoxy group, and wherein one to three methylene groups of the acyclic unsaturated hydrocarbon is optionally replaced with carbonyl groups), or a straight-chain or branched-chain saturated or unsaturated hydrocarbon containing from one to five thioether, ether, and/or amino bonds and having form 1 to 14 carbon atoms (wherein no hetero atoms are bonded directly to A, and one to three methylene groups of the hydrocarbon is optionally replaced with carbonyl groups); and $R^5$ is a hydrogen atom or an organic group having a basic skeleton selected from the group consisting of the following basic formulas:

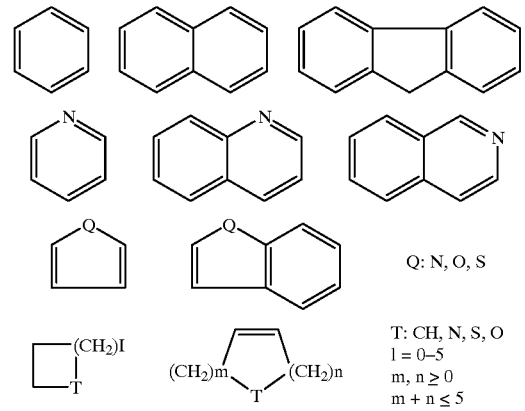

organic groups represented by $R^5$
wherein the organic group has optionally at least one substituent selected from the group consisting of an alkyl group having from 1 to 5 carbon atoms, an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, an isothiocyanate group, a trifluoromethyl group, a trifluoromethoxy group, and a methylenedioxy group; $R^6$ is a hydrogen atom, an alkyl group having from 1 to 5 carbon atoms, or an alkanoyl group having from 1 to 5 carbon atoms.

11. The method for stabilizing the 4,5-epoxy-morphinan derivative according to claim 10, wherein in the general formula (I), $R^1$ is a methyl group, an ethyl group, a propyl group, a butyl group, an isobutyl group, a cyclopropylmethyl group, an allyl group, a benzyl group, or a phenethyl group; $R^2$ and $R^3$ are, independently of one another, a hydrogen atom, a hydroxy group, an acetoxy group, or a methoxy group; A is —N($R^4$)C(=O)—, —N($R^4$)C(=O)O—, —N($R^4$)—, or —N($R^4$)SO$_2$— (wherein $R^4$ is a hydrogen atom, or a straight-chain or branched-chain alkyl group having from 1 to 5 carbon atoms); B is a straight-chain alkylene group having from 1 to 3 carbon atoms, —CH=CH—, —C≡C—, —CH$_2$O— or CH$_2$S—; $R^5$ is the same as in claim 11; and $R^6$ is a hydrogen atom.

12. A method for stabilizing a 4,5-epoxy-morphinan derivative according to claim 11, wherein in the general formula (I), $R^5$ is a hydrogen atom or an organic group having a basic skeleton selected from the group consisting of the following basic formulas:

  Q: O, S

Organic Groups Represented by $R^5$ wherein the organic group is optionally substituted with one or more substituents selected from the group consisting of an alkyl group having from 1 to 5 carbon atoms, an alkoxy group having from 1 to 5 carbon atoms, an alkanoyloxy group having from 1 to 5 carbon atoms, a hydroxy group, a fluorine atom, a chlorine atom, a bromine atom, an iodine atom, an amino group, a nitro group, a cyano group, an isothiocyanate group, a trifluoromethyl group, a trifluoromethoxy group, and a methylenedioxy group.

13. A method for stabilizing a 4,5-epoxy-morphinan derivative according to claim 12, wherein in the general formula (I), $R^1$ is a cyclopropylmethyl group or an allyl group; A is —N($R^4$)C(=O)— or —N($R^4$)C(=O)O— (wherein $R^4$ is a hydrogen atom, or a straight-chain or branched-chain alkyl group having from 1 to 5 carbon atoms); and B is a straight-chain alkylene group having from 1 to 3 carbon atoms, —CH=CH—, or —C≡C—.

* * * * *